United States Patent
Nüesch

(10) Patent No.: US 6,355,012 B1
(45) Date of Patent: Mar. 12, 2002

(54) BREAST MILK PUMP

(75) Inventor: Heinrich Nüesch, Zuzwil (CH)

(73) Assignee: Nüesch Logistik, Zuzwil (CH)

( * ) Notice: Subject to any disclaimer, the term of this patent is extended or adjusted under 35 U.S.C. 154(b) by 0 days.

(21) Appl. No.: 09/341,384

(22) PCT Filed: Jan. 8, 1998

(86) PCT No.: PCT/CH98/00006

§ 371 Date: Jul. 7, 1999

§ 102(e) Date: Jul. 7, 1999

(87) PCT Pub. No.: WO98/30257

PCT Pub. Date: Jul. 16, 1998

(30) Foreign Application Priority Data

Jan. 10, 1997 (DE) ......................................... 197 00 545

(51) Int. Cl.[7] .............................................. A61M 1/06
(52) U.S. Cl. ......................................... 604/74; 604/119
(58) Field of Search ............................ 604/74–76, 120, 604/131, 151, 152, 118, 119, 346; 417/534–536

(56) References Cited

U.S. PATENT DOCUMENTS 5,810,772 A * 9/1998 Niederberger ............... 604/74
5,954,690 A * 9/1999 Larsson ........................ 604/74
6,045,529 A * 4/2000 Nuesch ......................... 604/74

FOREIGN PATENT DOCUMENTS

EP 0744180 11/1996

* cited by examiner

Primary Examiner—Anhtuan T. Nguyen
(74) Attorney, Agent, or Firm—Martin A. Farber

(57) ABSTRACT

A breast pump for connection to a pair of funnel-like breast bodies via a corresponding pair of vacuum conduits in order to pump mother's milk into a milk collection container, the pump comprising a source of vacuum including pumping devices. A conduit system leads from the vacuum source at one end and comprises a pair of connection portions to be connected to the vacuum conduits at the other end. A pair of valve devices are arranged within the conduit system to distribute the vacuum to the connection portions, the pair of valve devices including a pair of valve bodies separated from each other so as to move independently from each other, a pair of valve chambers each housing one of the pair of valve bodies and each having an inlet opening communicating with the source of vacuum, and an outlet opening communicating with one of the pair of connection portions. Actuating devices for actuating the pair of valve bodies in a synchronized manner alternate from an open position, in which it connects the inlet opening and the outlet opening, to a closed position in which communication between the openings are interrupted.

11 Claims, 3 Drawing Sheets

BREAST MILK PUMP

FIELD AND BACKGROUND OF THE INVENTION

Using the known breast milk pump, simultaneous and gentle sucking from both breasts is achieved, wherein the drive may be effected in an electrical way, e.g. using a battery as a source of energy. Sucking is effected in a cyclic manner at about the natural rhythm of a sucking baby, and cycle periods of both breasts alternate so that the source of energy is not subjected to irregular load. In maximum, the cycle frequency should amount to about 60 per minute, but practice has shown that such a high frequency is difficult to achieve with the known breast milk pump. In addition, in order to avoid synchronizing both valves, the common drive actuates a common valve member which tends to produce a clattering noise at high velocities. This is, not least, to be put down to the fact that an adjustment of the individual valves is hardly possible for which reason the arrangement is relative sensitive to tolerances in production, i.e. too large a tolerance can lead to a situation wherein one valve does not yet close, while the other one is already open, or that there are periods in which both valves close so that the desirable uniform load of the source of energy is not given under all circumstances.

SUMMARY OF THE INVENTION

Therefore, it is an object of the invention to avoid at least part of the above disadvantages, and this is achieved, according to the invention, by the characteristic features of with such a breast milk pump.

By the fact that the drive continues to be common, synchronizing the two valves remains unnecessary as up to now. By the fact, however, that a respective valve member is provided, i.e. that the valve members are separated from each other, their inertia is reduced, which reduces also the clattering tendency, while it is easier at the same time to even out production tolerances, e.g. by selecting the separate valve members.

An especially preferred embodiment is described in provided. Such an embodiment reduces the sensitivity to tolerances, on the one hand, leads to improved sealing and, finally, enables also an embodiment according to claim 4.

BRIEF DESCRIPTION OF THE DRAWINGS

Further details of the invention will become apparent from the following description of embodiments schematically shown in the drawings, wherein FIG. 1 is an axonometric representation of a breast milk pump according to the invention of which

DETAILED DESCRIPTION OF THE PREFERRED EMBODIMENTS

Figure 1:
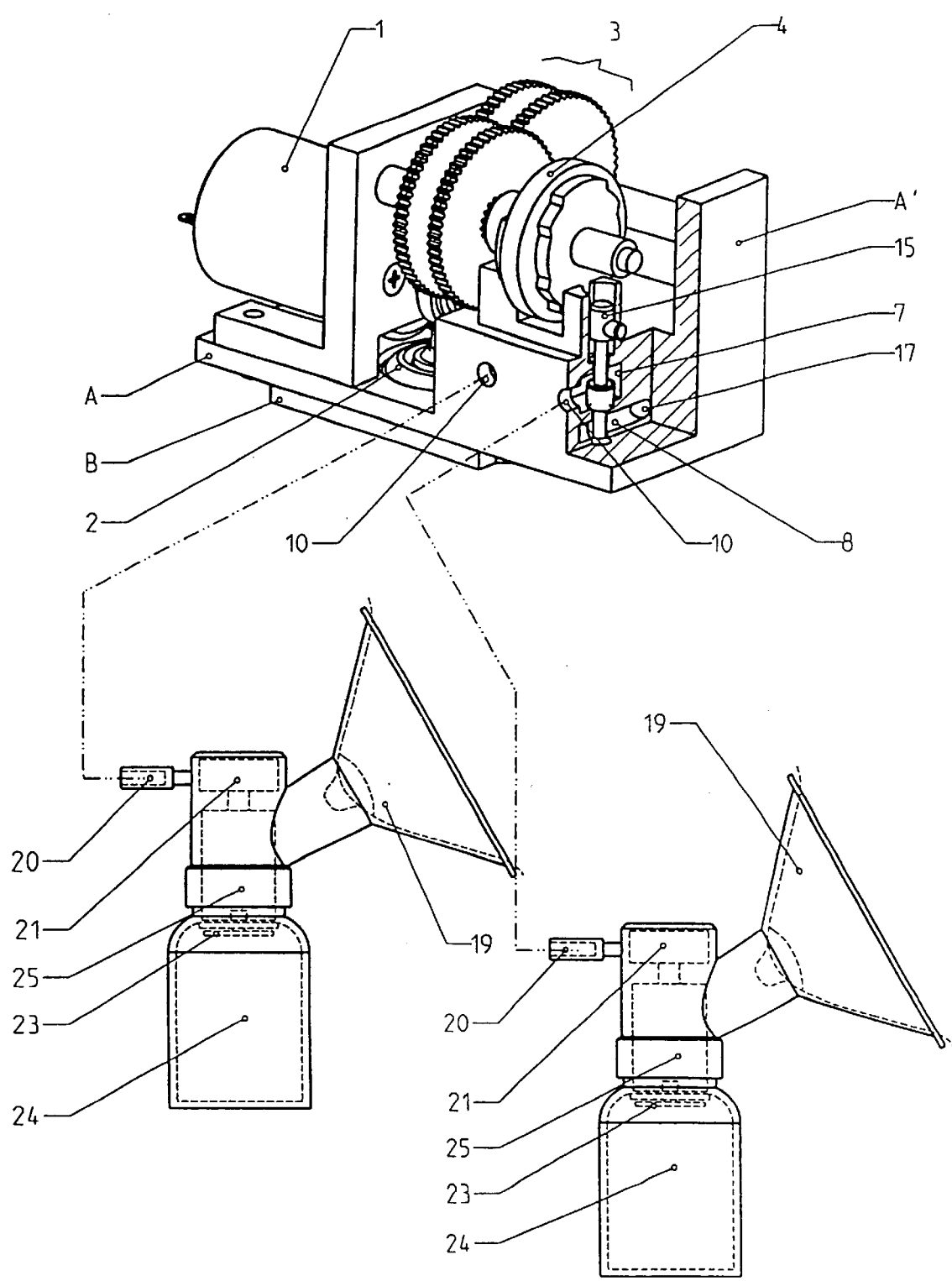

As in the above-mentioned prior art, an electric motor 1, being connected to a component carrier A, which comprises an end and support wall A', drives, as in the cited prior art, a diaphragm pump 2 (or any other pump) at a vacuum space B, on the one hand, and a reduction gear 3, on the other hand. In this respect, reference is made to the EP-A-0 744 180 already mentioned, the contents of which are incorporated by reference herein The reduction gear 3 is connected through a positive coupling 5 to a valve drive in form of a cam disk 4. This cam disk 4 has two cam profiles 4' formed in such a manner that two tappet-like valve members 15 (cf. FIG. 2) are moved in opposite direction to each other. In the present case, the valve tappets 15, which comprise cam follower pins 11 penetrating them, engage the outer surface of cams 4' under the pressure of springs 6. Optionally, a positive guidance by a cam groove can also be provided for the cam followers, as will be described later with reference to FIG. 3.

While one end of the cam follower 11 engages the respective cam 4', the other end 11' is preferably guided in a vertical groove 13 so that turning of the valve tappet 15 is prevented. Concurrently, due to this about cruciform shape of a valve shaft 12 and the cam follower pin 11, one of the ends of the respective pressure spring 6 can prop against it, while the other end is at the bottom of an enlarged bore 14. The cam follower pin 11 penetrates a broadened head 15" of the valve tappet 15. This head 15" may be screwed onto the shaft 12 so that the individual position of the valve member is adjustable relative to the valve chamber or a piston portion 15' with respect to the drive 4 for each of the two valves illustrated.

Figure 2:
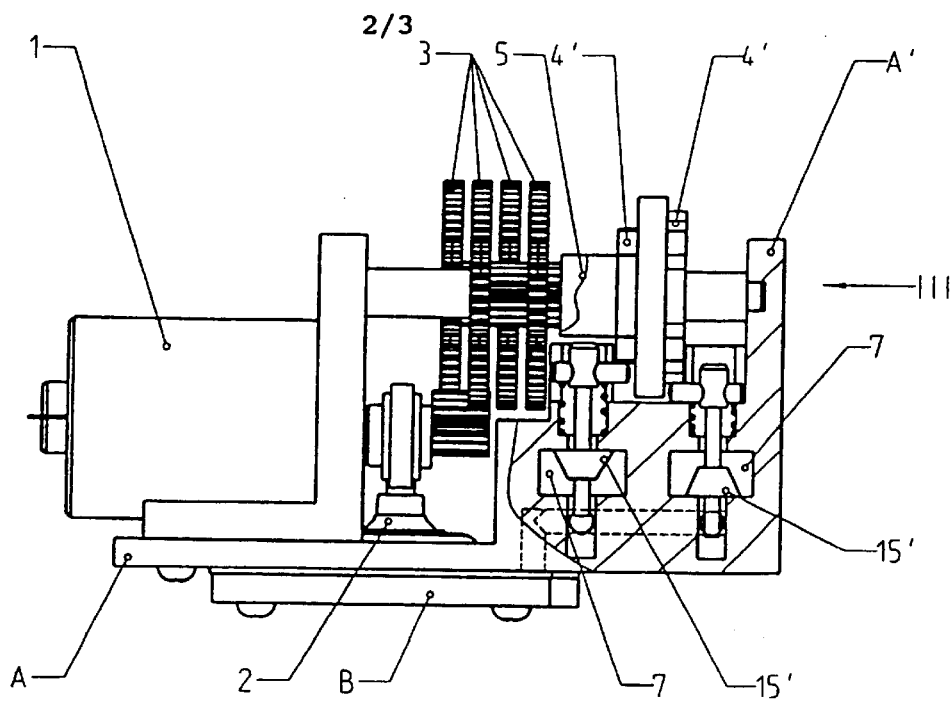
FIG. 2 shows a lateral view, partly in cross-section.
Figure 2A:
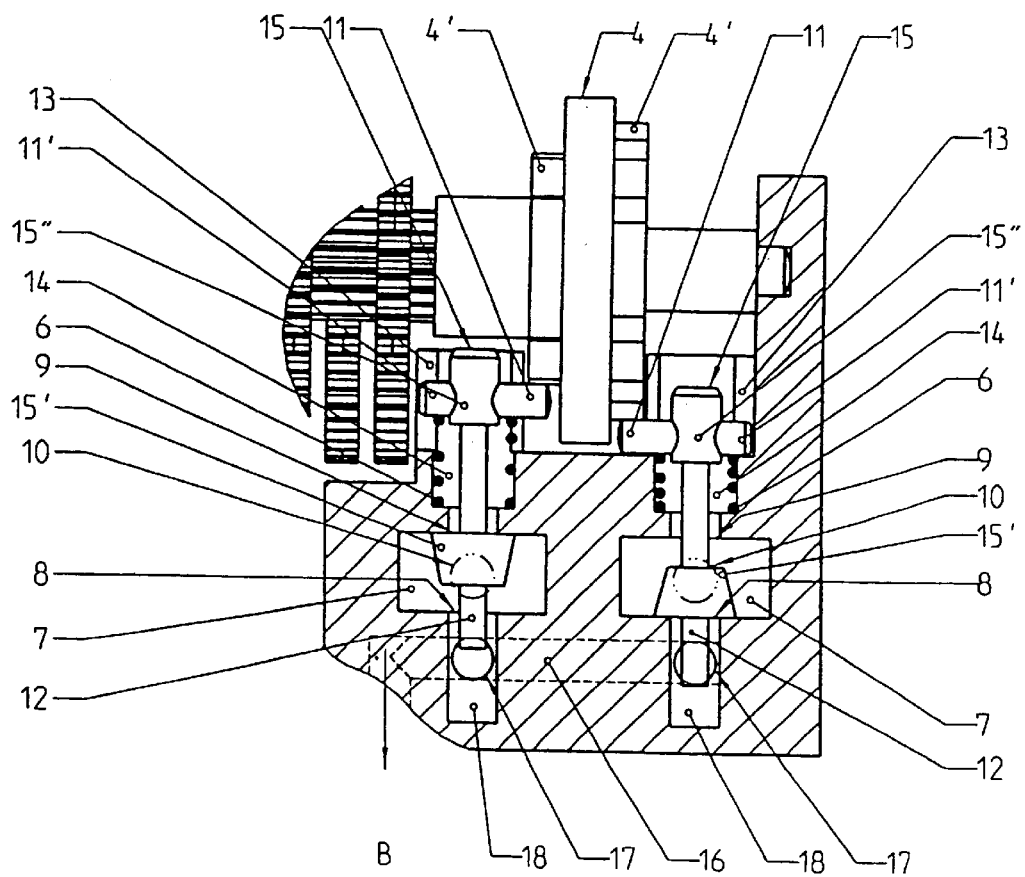
FIG. 2A illustrates part of FIG. 2 at a larger scale showing the valves in detail.

Each valve tappet 15 has a such a piston-like sealing element 15' attached to the shaft 12. This piston portion 15' is preferably made of elastic material, such as silicone rubber, and is, thus, compressible. When this piston portion 15' is relieved, as corresponds to an especially preferred embodiment, its axial extension, i.e. its height when seen in FIG. 2, is at least as large, optionally even somewhat larger, than the dimension of the valve chamber 7, in which it is moveable, in the same direction. The piston portion 15', however, forms in both of its extreme positions shown in FIG. 2, an elastically compressed bulge 15" at top or at the bottom. For facilitating this effect, it may be advantageous, if the piston portion 15' is connected to the valve shaft 12 only at its axial center so that its axial ends are free.

A channel 16 communicates with the vacuum space B and has an outlet 17 in the region of each valve chamber 7. Since the valve shaft 12 is thinner than the bore 18, which surrounds it, there is an annular space between it and the inner surface of this bore 18 which respectively communicates with the outlet 17. The bore 18 leads from an entrance 8 into the valve chamber 7 from which a horizontal outlet bore 10 leads out. As shown in FIG. 1, a hose 20 can each be connected to these outlet bores 10 and leads to a suction chamber 21 as well as to the breast body 19. A milk collection container 24 is connected via a non-return valve 23 for separating a suction chamber 25.

By the above-mentioned especially preferred embodiment comprising the elastic large piston portion 15', three different control positions of the valve are enabled, as described in the following.

In an open position, the piston portion 15' opens the entrance 8 from the bore 18 to the valve chamber 7 so that the latter is subjected to suction pressure from the vacuum space B below the diaphragm pump 2. This position is illustrated in FIG. 2 making reference to the left-hand valve. In this position, the related outlet bore 10 is freed by the piston portion 15' so that suction pressure acts also upon this bore 10 and the connected hose 20. At the same time, the piston portion 15' closes an venting opening 9 at the upper side of the valve chamber 7, i.e. opposite the entrance opening 8. This venting opening 9 serves to reduce the suction pressure relative quickly at the end of a suction cycle, because the outlet bore 10 can communicate with the venting opening 9 during the stroke of the piston portion from the left position of FIG. 2 into the right position, in case the construction discussed later on for such an intermediate position is not provided.

In the closed position shown in FIG. 2 with reference to the right-hand valve, the piston portion 15' is pressed firmly against the entrance opening 8, forming the bulge 15" already mentioned, and closes optionally also the outlet bore 10, as shown. This outlet bore 10, however, is situated, as shown in FIG. 2, partially above the bulge 15" so that communication to the venting opening 9 may be provided, if desired. The extent of such a communication and, thus, of the relief of the suction pressure at the respective breast body 19 (cf. FIG. 1) can be adjusted by the arrangement of the outlet bore 10 relative to the valve chamber 7. In any case, however, the entrance 8 is separated from the outlet 10 in the closed position; but if a venting opening 9 is arranged, as is preferred, the outlet 10 communicates with it so that the suction pressure, which acts upon the breast body 19 (FIG. 1), is practically abruptly relieved.

In FIG. 2, the outlet bore 10 is at half the height of the valve chamber 7, and stronger or quicker venting can be achieved by locating the outlet bore 10 at a higher or lower place. However, an embodiment is also conceivable in which the chamber wall, which comprises the outlet bore 10, is formed as a slider adjustable in height and having an opening as the outlet bore which opens into an enlarged outlet space of the component carrier A. By shifting such a slider, the sucking or the venting effect can be adjusted individually.

It has already been mentioned above that the axial dimension, i.e. with reference to FIG. 2 the height, of the piston portion 15' may be preferably at least equal to or optionally even somewhat larger than the axial dimension of the valve chamber 7. If this is the case, the piston portion will practically close all the openings 8, 9 and 10 in an intermediate position in-between the positions shown in FIG. 2. Since the entrance opening 8 communicated with the outlet bore 10 shortly before, suction pressure will be present at the latter as before and can be relieved but slowly, e.g. by leakage air entering at the breast body 19.

This means, however, that in such an embodiment the suction pressure is longer acting as would be the case, if the piston portion 15' were smaller or inelastic. And this means that the energy introduced by the motor 1 can be better utilized and, therefore, the valve member 15 can return earlier into its closed position (FIG. 2 at right), because suction pressure is still maintained for a while. This, however, enables a higher frequency of cycles, as, although being aimed in the prior art, was never reached in practice. Thus, pumping the milk off continues to be effected in an alternating manner treating the battery with care, but there are overlapping periods in which the suction pressure is still present at the breast body 19, while beginning already sucking the other breast body.

From the above explanation, it can be seen that the arrangement of three openings 8, 9 and 10 to the valve chamber 7 is basically of advantage and results in novel function characteristics and facilities so that this aspect represents an invention of its own independent from the use of separate valve members or of a common valve member (as in the prior art).

Figure 3:
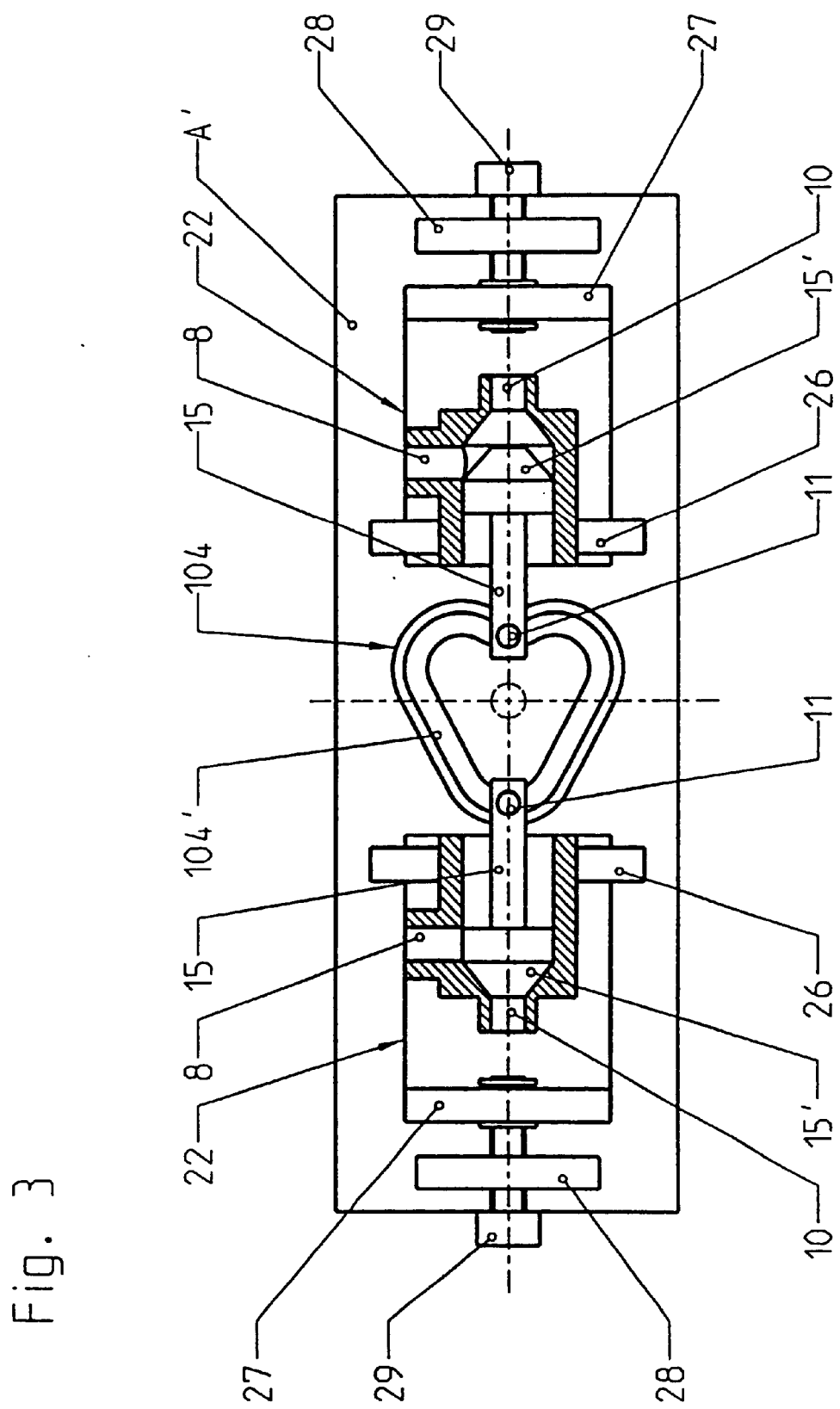
FIG. 3 is a view in the direction of arrow III of FIG. 2, but of another embodiment.

While the valve members 15 are parallel to each other in the embodiment of FIGS. 1 and 2, FIG. 3 shows that other arrangements are also possible. In this case, a common positive cam 104 having a cam guidance formed as a groove 104' is situated at the outer surface of wall A'. Again cam followers 11 engage this groove 104'. The cam 104 is formed as a cardioid, as shown, as is common in textile industry for generating a reciprocating movement. Thus, the valve members 15 situated opposite to one another will move in opposite direction with respect to their assigned valve housing 107.

The valve housing is designed in the manner of so-called cartridge valves which are generally formed as ON-OFF-valves, i.e. as switching valves. It should be mentioned, however, that it is also known to design such valves as proportional valves which should, likewise, not be excluded within the scope of this invention. In any case, the construction as a cartridge valve means, that a lateral entrance 8 is provided, for example, and an axial outlet 10 cooperating with a piston portion 15', e.g. elastic again. Of course, also in this case a venting opening may be provided in the housing 107, if desired.

In order to be able to adapt and adjust individually, each of the housings 107 is supported on a plate 22. By attaching the housings 107 on the respective plate 22, e.g. by adhesive, at a selected distance to the gear shaft 3', an individual adjustment of the open and closed periods can be achieved.

It is preferred, however, to guide the plates 22 displaceably on the wall A' by means of gradually projecting guidances 26, thus forming a kind of adjustment slide that is provided with an angled wall 27 at one end. From wall A', however, stationary, e.g. run in, tabs 28 project outwards. Adjustment screws 29 accessible from outside are connected to the angled wall 27 in an axially indisplaceable, but rotatable manner and are, at the same time, screwed into an inner thread of the respective tab 28. Thus, by turning the screws 29, the relative distance of valve housing 107, valve member 15 and drive 104 can be adjusted in an analogous way, as described above for the preceding embodiment with reference to the screw heads 15". This is, of course, enabled by separating the two valve members 15 in accordance with the invention maintaining a common drive 104.

Numerous variations are conceivable within the scope of the invention; for example, the sealing element 15 needs not to be in piston-like shape, because, in the case of FIGS. 1 and 2, only the region of the elastic bulges 15" is pressed sealingly against the respective opening 8 or 9. With the same benefit, only these bulges 15" could be replaced by elastic disk seats suitably concavely domed towards the respective opening.

I claim:

1. A breast pump for connection to a pair of funnel-like breast bodies via a corresponding pair of vacuum conduits in order to pump mother's milk into a milk collection container, the pump comprising:

a source of vacuum including pumping means;

a conduit system leading from said vacuum source at one end and comprising a pair of connection portions to be connected to said vacuum conduits at the other end;

a pair of valve means arranged within said conduit system to distribute said vacuum to said connection portions, said pair of valve means including a pair of valve bodies separated from each other so as to move independently from each other, a pair of valve chambers each housing one of said pair of valve bodies and each having an inlet opening communicating with said source of vacuum, and an outlet opening communicating with one of said pair of connection portions; and actuating means for actuating said pair of valve bodies in a synchronized manner alternating from an open position, in which it connects said inlet opening and said outlet opening, to a closed position in which communication between said openings is interrupted.

2. Breast pump as claimed in claim 1, wherein said pumping means comprise electric motor means.

3. Breast pump as claimed in claim 1, wherein said pair of valve chambers are substantially symmetrically arranged with respect to said actuating means.

4. Breast pump as claimed in claim 1, further comprising adjusting means for adjusting the relative position of at least one of said valve chambers, valve bodies and actuating means.

5. Breast pump for connection to a pair of funnel-like breast bodies via a corresponding pair of vacuum conduits in order to pump mother's milk into a milk collection container, the pump comprising:

a source of vacuum including pumping means;

a conduit system leading from said vacuum source at one end and comprising a pair of connection portions to be connected to said vacuum conduits at the other end;

a pair of valve means arranged within said conduit system to distribute said vacuum to said connection portions, said pair of valve means including a pair of valve bodies separated from each other so as to move independently from each other, a pair of valve chambers each housing one of said pair of valve bodies and each having an inlet opening communicating with said source of vacuum, and an outlet opening communicating with one of said pair of connection portions; and actuating means for actuating said pair of valve bodies in a synchronized manner alternating from an open position in which it connects said inlet opening and said outlet opening, to a closed position in which communication between said openings is interrupted;

wherein said pair of valve bodies comprises each an elongated shaft having an actuation end connected to said actuating means, and a broadened portion located offset from said actuation end, serving as a sealing member for sealing one of said openings in one of its positions and being formed of an elastic material at least in part.

6. Breast pump as claimed in claim 5, wherein said sealing member is shaped as a plunger.

7. Breast pump as claimed in claim 5, wherein said elastic material is a silicone rubber.

8. Breast pump as claimed in claim 5, wherein said sealing member of elastic material, in incompressed state, fills at least a major part of its valve chamber so that, when actuated by said actuating means, it assumes an open position, a closed position and an intermediate position closing both the inlet and the outlet of its valve chamber.

9. Breast pump as claimed in claim 5, wherein each of said valve chambers comprises a venting opening leading to ambient air for reducing vacuum pressure, said venting opening being situated so as to be closed by the associated valve body in the open position of the valve body.

10. Breast pump as claimed in claim 9, wherein said venting opening is situated opposite said inlet opening.

11. Breast pump as claimed in claim 5, further comprising adjusting means for adjusting the relative position of at least one of said valve chambers, valve bodies and actuating means.

* * * * *